United States Patent
Bouboulis

(10) Patent No.: US 10,463,872 B2
(45) Date of Patent: Nov. 5, 2019

(54) DEVICE AND METHOD FOR TREATING ALLERGIC RHINITIS

(71) Applicant: LUMIMED, LLC, Darien, CT (US)

(72) Inventor: Denis Bouboulis, Darien, CT (US)

(73) Assignee: Lumimed, LLC, Darien, CT (US)

( * ) Notice: Subject to any disclaimer, the term of this patent is extended or adjusted under 35 U.S.C. 154(b) by 0 days.

(21) Appl. No.: 15/048,359

(22) Filed: Feb. 19, 2016

(65) Prior Publication Data
US 2016/0166848 A1    Jun. 16, 2016

Related U.S. Application Data

(63) Continuation of application No. 13/204,282, filed on Aug. 5, 2011, now Pat. No. 9,265,967.

(51) Int. Cl.
*A61N 5/06* (2006.01)
*A61N 5/067* (2006.01)

(52) U.S. Cl.
CPC ......... *A61N 5/0603* (2013.01); *A61N 5/0613* (2013.01); *A61N 2005/063* (2013.01);
(Continued)

(58) Field of Classification Search
CPC ........ A61N 5/062; A61N 5/603; A61N 5/613; A61N 2005/607; A61N 2005/626; A61N 2005/63; A61N 2005/644; A61N 2005/651; A61N 2005/654; A61N 2005/659; A61N 2005/663; A61N 2005/667; A61N 2005/67; A61N 5/0603; A61N 5/061; A61N 2005/0607; A61N 2005/0626; A61N 2005/063; A61N 2005/0644; A61N 2005/0651; A61N 2005/0654;
(Continued)

(56) References Cited

U.S. PATENT DOCUMENTS

| 1,706,161 A | 3/1929 | Hollnagle |
| 5,001,608 A | 3/1991 | Kehrli et al. |
| (Continued) | | |

FOREIGN PATENT DOCUMENTS

GB    2 212 010    7/1989

OTHER PUBLICATIONS

Emberlin et al.; "Pollen challenge study of a phototherapy device for reducing the symptoms of hay fever", Current Medical Research and Opinion, vol. 25, No. 7, 2009, pp. 1635-1644.
(Continued)

*Primary Examiner* — Michael W Kahelin
*Assistant Examiner* — Wynn V Huh
(74) *Attorney, Agent, or Firm* — Ohlandt, Greeley, Ruggiero & Perle, L.L.P.

(57) ABSTRACT

A device for delivering light to a nasal cavity is provided. The device has a base at a proximal end of the device. The base has a first end that is the proximal end and a second end opposite the first end. The device also has a sleeve operably connected to the base at the second end, an endpiece connected to the sleeve at a joint, a tapered tip for insertion into the nasal cavity, a light source disposed inside the tapered tip, and a power source to supply power to the device. The endpiece moves in the sleeve during pivoting movement about the joint. The angle between the sleeve and the endpiece is changeable from 0° to 40°.

20 Claims, 16 Drawing Sheets

(52) U.S. Cl.
CPC ............... *A61N 2005/0607* (2013.01); *A61N 2005/067* (2013.01); *A61N 2005/0626* (2013.01); *A61N 2005/0644* (2013.01); *A61N 2005/0651* (2013.01); *A61N 2005/0654* (2013.01); *A61N 2005/0659* (2013.01); *A61N 2005/0663* (2013.01); *A61N 2005/0667* (2013.01)

(58) Field of Classification Search
CPC .... A61N 2005/0659; A61N 2005/0663; A61N 2005/0667; A61N 2005/067
USPC ..................................................... 607/88–92
See application file for complete search history.

(56) References Cited

U.S. PATENT DOCUMENTS

| | | | | |
|---|---|---|---|---|
| 5,683,436 | A * | 11/1997 | Mendes | A61N 5/0603 |
| | | | | 607/88 |
| 6,358,272 | B1 | 3/2002 | Wilden | |
| 6,500,198 | B1 * | 12/2002 | Southard | A61N 5/0616 |
| | | | | 607/2 |
| 6,576,224 | B1 | 6/2003 | Osbakken et al. | |
| 6,764,501 | B2 | 7/2004 | Ganz | |
| 7,101,996 | B2 | 9/2006 | Skuratowicz | |
| 7,166,664 | B1 | 1/2007 | Anderson | |
| 7,226,470 | B2 | 6/2007 | Kemeny et al. | |
| D569,987 | S | 5/2008 | Oberreiter et al. | |
| 7,435,252 | B2 | 10/2008 | Krespi et al. | |
| D589,154 | S | 3/2009 | Oberreiter et al. | |
| 7,517,344 | B2 | 4/2009 | Van Hal et al. | |
| 7,544,204 | B2 | 6/2009 | Krespi et al. | |
| D596,748 | S | 7/2009 | Oberreiter et al. | |
| D621,950 | S | 8/2010 | Seki et al. | |
| D635,271 | S | 3/2011 | Azar et al. | |
| 2004/0030368 | A1 * | 2/2004 | Kemeny | A61N 5/0603 |
| | | | | 607/88 |
| 2004/0116985 | A1 | 6/2004 | Black | |
| 2004/0171970 | A1 * | 9/2004 | Schleuniger | A61B 8/546 |
| | | | | 601/2 |
| 2004/0206365 | A1 | 10/2004 | Knowlton | |
| 2006/0074468 | A1 * | 4/2006 | Neev | A61B 18/203 |
| | | | | 607/90 |
| 2006/0111760 | A1 | 5/2006 | Kemeny et al. | |
| 2006/0136019 | A1 | 6/2006 | Kemeny et al. | |
| 2006/0155349 | A1 | 7/2006 | Kemeny et al. | |
| 2006/0167531 | A1 * | 7/2006 | Gertner | A61N 5/0603 |
| | | | | 607/86 |
| 2006/0195165 | A1 | 8/2006 | Gertner et al. | |
| 2006/0235492 | A1 | 10/2006 | Kemeny et al. | |
| 2006/0271024 | A1 | 11/2006 | Gertner et al. | |
| 2006/0292182 | A1 | 12/2006 | Kemeny et al. | |
| 2007/0038206 | A1 * | 2/2007 | Altshuler | A46B 15/0036 |
| | | | | 606/20 |
| 2007/0219600 | A1 | 9/2007 | Gertner et al. | |
| 2007/0255357 | A1 | 11/2007 | Rose et al. | |
| 2008/0033512 | A1 | 2/2008 | Yu | |
| 2008/0077204 | A1 | 3/2008 | Bornstein | |
| 2008/0108982 | A1 * | 5/2008 | Barolet | A61B 18/203 |
| | | | | 606/9 |
| 2008/0140164 | A1 | 6/2008 | Oberreiter et al. | |
| 2008/0208297 | A1 | 8/2008 | Gertner et al. | |
| 2008/0221646 | A1 | 9/2008 | DiMauro et al. | |
| 2009/0018485 | A1 | 1/2009 | Krespi et al. | |
| 2009/0093865 | A1 * | 4/2009 | Krespi | A61N 5/0603 |
| | | | | 607/88 |
| 2009/0143842 | A1 * | 6/2009 | Cumbie | A61N 5/0616 |
| | | | | 607/88 |
| 2009/0222068 | A1 | 9/2009 | Oberreiter et al. | |
| 2010/0155201 | A1 * | 6/2010 | Zuluaga | H01H 1/242 |
| | | | | 200/11 J |
| 2010/0222852 | A1 | 9/2010 | Vasily et al. | |
| 2011/0152977 | A1 | 6/2011 | Sueyoshi et al. | |
| 2012/0008311 | A1 * | 1/2012 | Opolka | F21L 4/005 |
| | | | | 362/157 |
| 2014/0207214 | A1 * | 7/2014 | Oberreiter | A61N 5/0603 |
| | | | | 607/92 |

OTHER PUBLICATIONS

Koreck et al.; "Rhinophototherapy: A new therapeutic tool for the management of allergic rhinitis", J. Allergy Clin. Immunol., Mar. 2005, pp. 541-547.
Neuman et al.; "Narrow-band red light phototherapy in perennial allergic rhinitis and nasal polyposis"; Annals of Allergy, Asthma & Immunology, vol. 78, Apr. 1997, pp. 399-406.
International Search Report dated Oct. 16, 2012 from corresponding International Patent Application No. PCT/US2012/049108, 4 pages.
Written Opinion dated Oct. 16, 2012 from corresponding International Patent Application No. PCT/US2012/049108, 11 pages.
Supplementary European Search Report dated Nov. 21, 2014 from corresponding European Application No. 12821600.9, 6 pages.
Lindsey, Heather; "Rhinophototherapy May Offer Promise to Allergic Rhinitis Patients", ENT Today, Mar. 2007, p. 22.
http://www.intelligenthealthysystems.com.au/bionase/, Aug. 4, 2011, 6 pages.

* cited by examiner

DEVICE AND METHOD FOR TREATING ALLERGIC RHINITIS

CROSS REFERENCE TO RELATED APPLICATION

This application is a continuation of U.S. patent application Ser. No. 13/204,282, filed on Aug. 5, 2011, the entire contents of all of which are incorporated by reference herein.

BACKGROUND OF THE DISCLOSURE

1. Field of the Disclosure

This disclosure relates to the use of phototherapy to treat the symptoms of seasonal and perennial allergic rhinitis.

2. Description of Related Art

Allergic rhinitis (also commonly known as hay fever) is a condition that occurs when allergens such as pollens cause inflammation of mucous membranes in the nose. Symptoms including sneezing, itching, nasal discharge, and/or congestion. Perennial and seasonal allergic rhinitis afflict millions of persons throughout the world.

Treatment of allergic rhinitis has traditionally been accomplished through the use of systemic medications, antihistamines, decongestants, steroids, and long-term immunotherapy. Each of these treatment modalities has advantages and disadvantages but typically no single modality or combination of modalities can completely relieve all of the symptoms of allergic rhinitis.

In contrast to and/or as a supplement to those traditional treatments, phototherapy has relatively recently been found to be effective in treating allergic rhinitis. Although phototherapy has been used for many years to treat various skin conditions (such as acne, psoriasis, pigmented lesions, and wounds, and to help tighten sagging skin, reduce wrinkles, and stimulate circulation, to name a few), and lasers have been used in surgical applications (including to treat various conditions in the nasal cavity such as legions, polyps etc.), studies have recently shown that phototherapy can also be used to help temporarily reduce or eliminate symptoms of allergic rhinitis. The present disclosure provides a convenient, safe, and affordable device and methodology for making available that treatment.

SUMMARY OF THE DISCLOSURE

The present disclosure provides for the utilization of phototherapy in the treatment of allergic rhinitis.

The present disclosure also provides a device that stimulates the human body's own respiratory system to reduce symptoms of allergic rhinitis.

The present disclosure further provides for a convenient and inexpensive device that enables allergy sufferers to be effectively treated.

The present disclosure also provides for a device that has a tapered tip for insertion into a nasal cavity and a light source within such tapered tip that is able to illuminate such nasal cavity for phototherapeutic treatment of rhinitis.

The present disclosure further provides for such a device that has a tapered tip for insertion into a nasal cavity and a light source that provides for circumferential light delivery within such tapered tip to maximize exposure of the nasal tissue to the light source.

The present disclosure also provides for a handheld apparatus for nasal application of phototherapy that has a straight portion and an adjustable portion. The adjustable portion has two parts that are movable relative to each other to form a hinge/joint that permits the user to adjust the angle of insertion of the tapered tip of the adjustable portion into the nasal cavity.

The present disclosure further provides for a safety feature that prevents activation of a light source for phototherapy treatment until after a circuit has been completed that indicates that nasal tip has been inserted into a nasal cavity of a user.

The present disclosure still further provides for a safety feature that is a contact switch having two curved portions that correspond to the curvature of the outer portion of a nostril. When such curved portions are depressed during insertion, a circuit is completed to permit activation of a light source in a nasal insertion tip for the treatment of rhinitis.

The present disclosure yet further provides for a methodology of treating rhinitis using phototherapy by illuminating a nasal cavity with light in the wavelength of from 600-950 nm. The light can be generated by a gas flashlamp, an IR light source, a laser diode, an LED, fiber optic cable or bundle other suitable means. The light is delivering in a quantity of from 12 to 24 joules/cm$^2$ of light energy. When the light is a flashlamp, a wavelength of from 600 nm to about 690 nm can be used although a range of from 650 nm to 660 nm is preferred. When infra-red light is used a range of from 700 nm to 950 nm can be used although a range of from about 700 to 900 is preferred.

A device for delivering light to a nasal cavity includes a base; an adjustable portion operably connected to the base. The adjustable portion permits ready manipulation of the device when in the nasal cavity. The adjustable portion includes a tapered tip for insertion into the nasal cavity; a light source disposed inside of the tapered tip; and a power source to supply power to the device.

A device for delivering light to a nasal cavity includes a housing having a tapered tip and two or more portions; and a joint that permits an angle to be formed between the two portions of the housing. The device also includes a light source disposed within the tapered tip for illumination of the nasal cavity; and a safety feature that restricts delivery of light from the light source to the nasal cavity. A power source to supply power to said housing.

A device for delivering light to a nasal cavity includes a housing having a tapered tip; and a light source inserted within the tapered tip to illuminate the nasal cavity. The device also includes a safety feature disposed on the housing that detects contact or pressure between the safety feature and a nostril of a user to enable illumination of the light source. The device provides a power source to supply power to the housing.

A method for treating rhinitis includes generating light in a wavelength of approximately 600 nm-950 nm; providing light to a user's nasal cavity by insertion of a light source, by inserting at least a portion of the light source into the nasal cavity; and delivering a dosage of approximately 12 to 24 Joules/cm2 of light energy to the user's nasal cavity. When the light source is a flashlamp, a wavelength of from 600 nm to about 690 nm can be used although a range of from 650 nm to 660 nm is preferred. When the light source is a infra-red light is used a range of from 700 nm to 950 nm can be used although a range of from 700 to 900 is preferred.

BRIEF DESCRIPTION OF THE DRAWINGS

FIG. 7b is a partial rendition of the device of FIG. 7a;

FIG. 7c is a partial rendition of the device of FIG. 7a;

FIG. 7d is an exploded view of the device of FIG. 7a;

DETAILED DESCRIPTION OF THE DISCLOSURE

Figure 1:
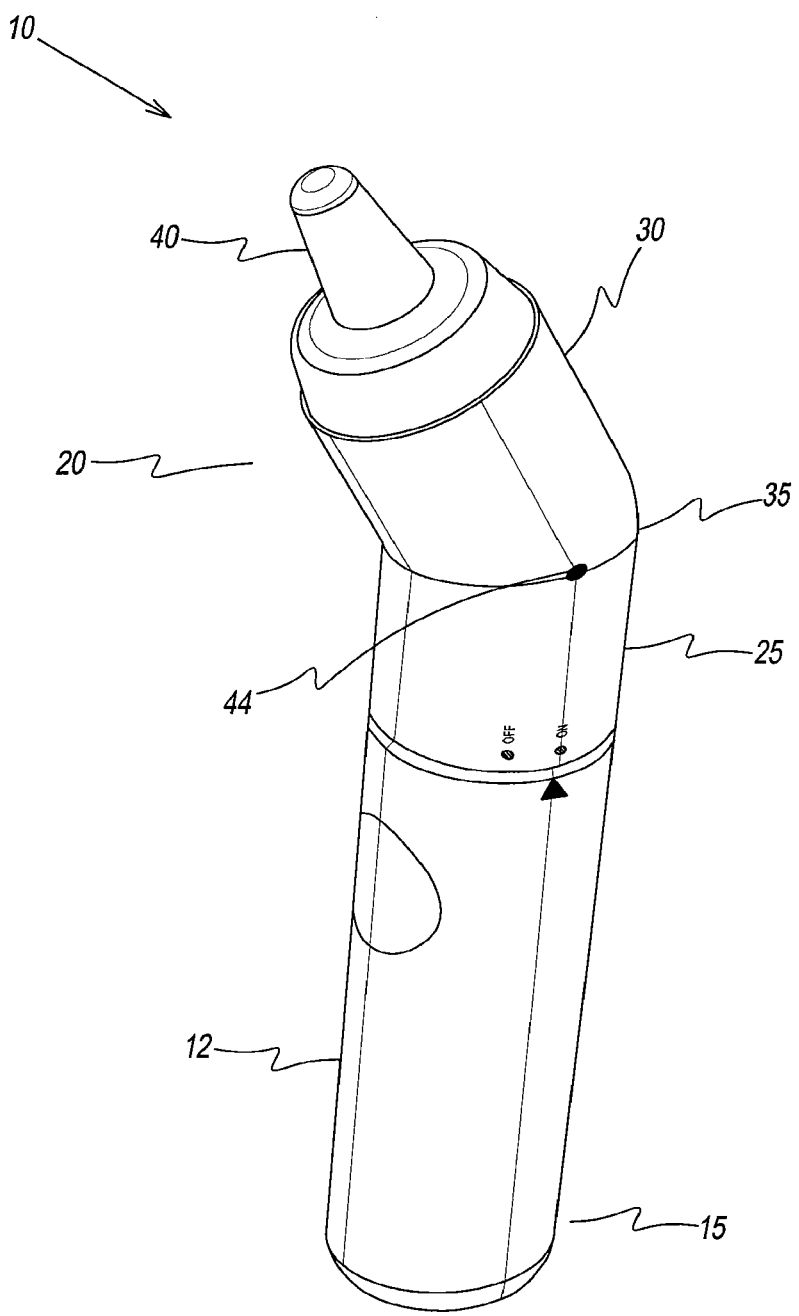
FIG. 1 is a perspective view of the device of the present disclosure in an angled configuration.
Figure 2:
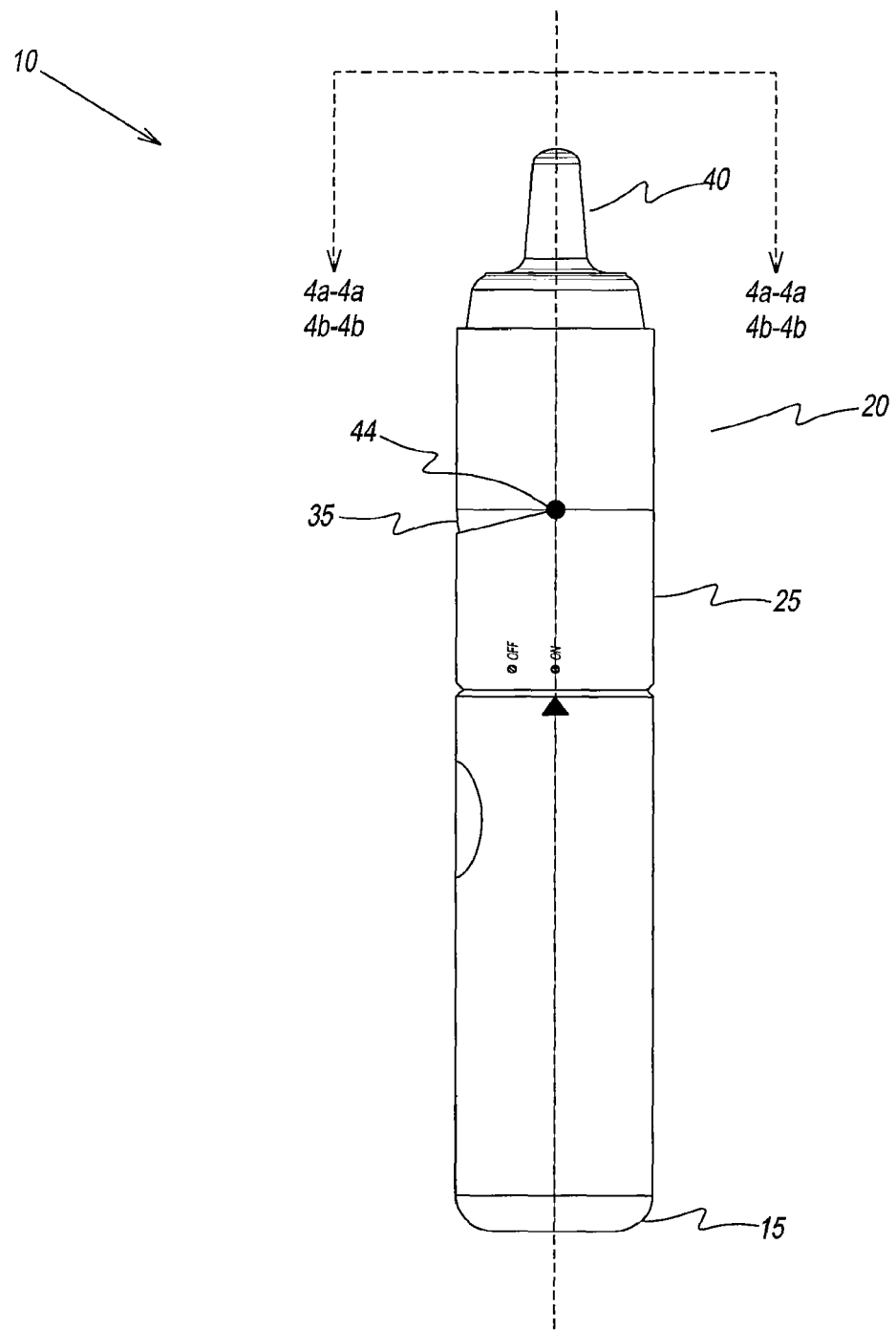
FIG. 2 is a side view of the device of FIG. 1 in a straight configuration.

Referring to the drawings and, in particular, to FIG. 1, a phototherapy device is shown and generally referenced by reference numeral 10. Device 10 has a housing 12 with a base 15 and an adjustable portion 20. Adjustable portion 20 includes a sleeve 25 and an endpiece 30. Endpiece 30 has a curved end 35 and an insertion tip 40. Insertion tip 40 contains a light source 70 as shown in FIG. 4 that may be activated to treat allergic rhinitis. Curved end 35 is secured to sleeve 25 to permit endpiece 30 to pivot relative to sleeve 25 about pivot points 44 (one shown). FIGS. 1 and 7 illustrate device 10 in an adjusted configuration with endpiece 30 pivoted about points 44 relative to sleeve 25.

FIGS. 2 and 4a through 4c illustrate device 10 in a straight configuration in which endpiece 30 is co-axial or in a non-bent configuration relative to sleeve 25. In the straight configuration, curved end 35 is partially shown and partially hidden inside of sleeve 25. Device 10 is preferably a handheld device for purposes of enhanced portability having an overall length of approximately 6 inches in a straight configuration.

Figure 3:
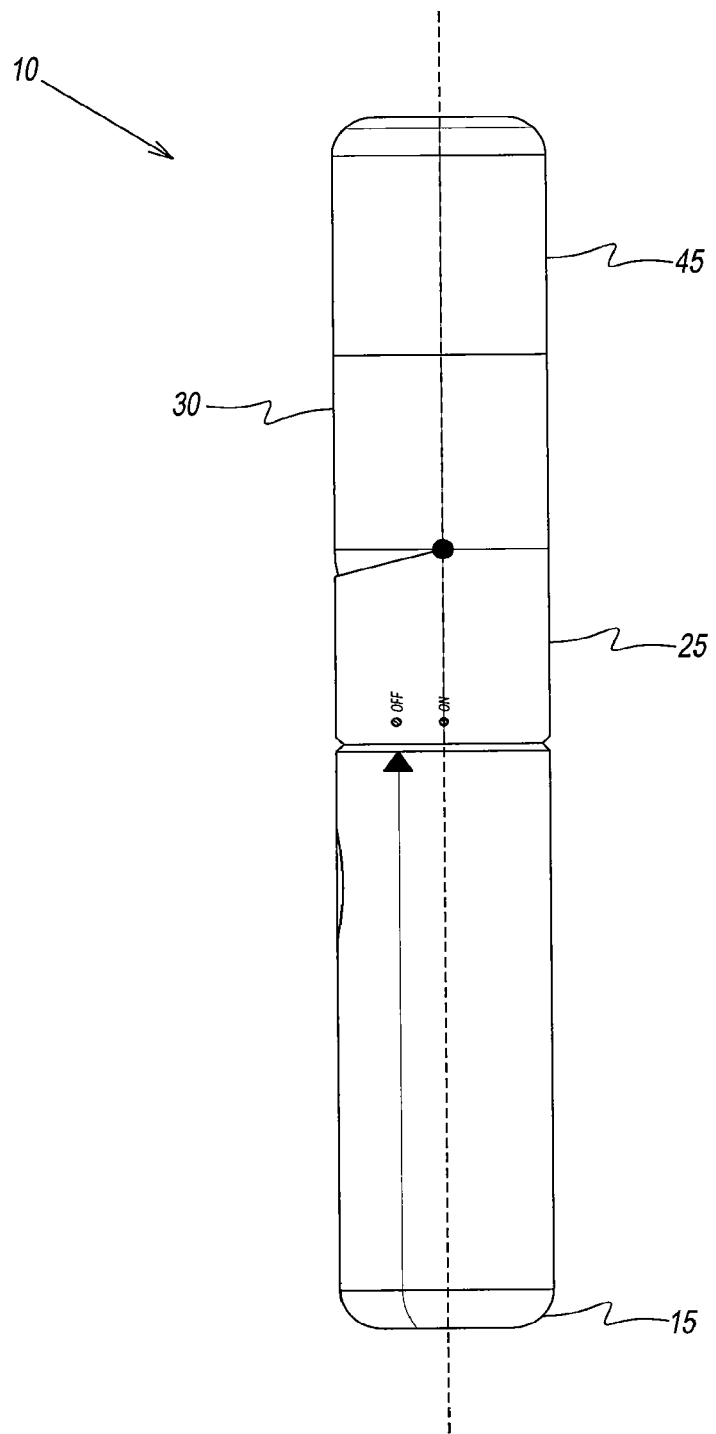
FIG. 3 is a side view of the device of FIG. 1 in a with a safety cap covering the nasal insertion tip.
Figure 4A:
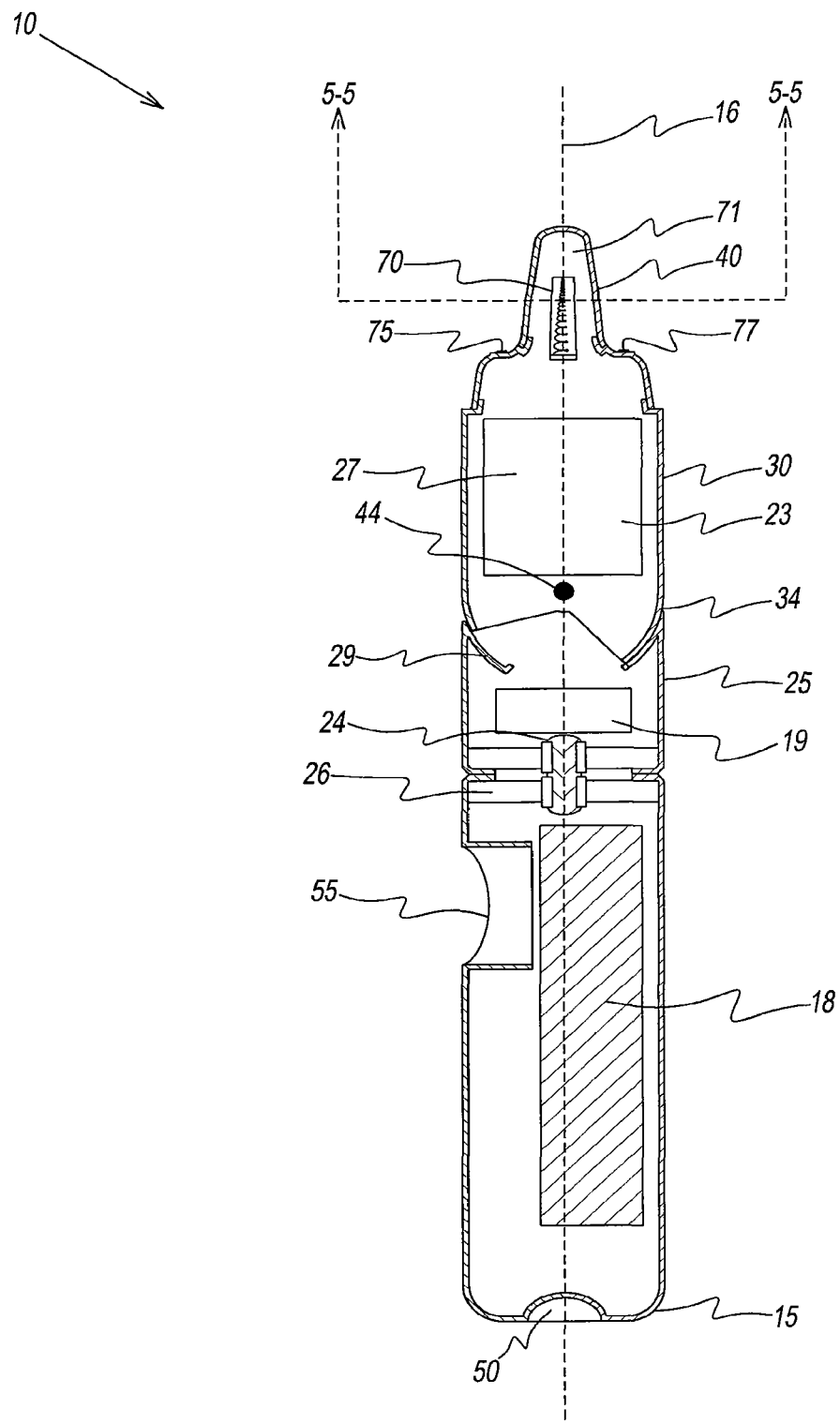
FIG. 4a is a cross-section view of the device taken along line 4a-4a of FIG. 1.
Figure 4B:
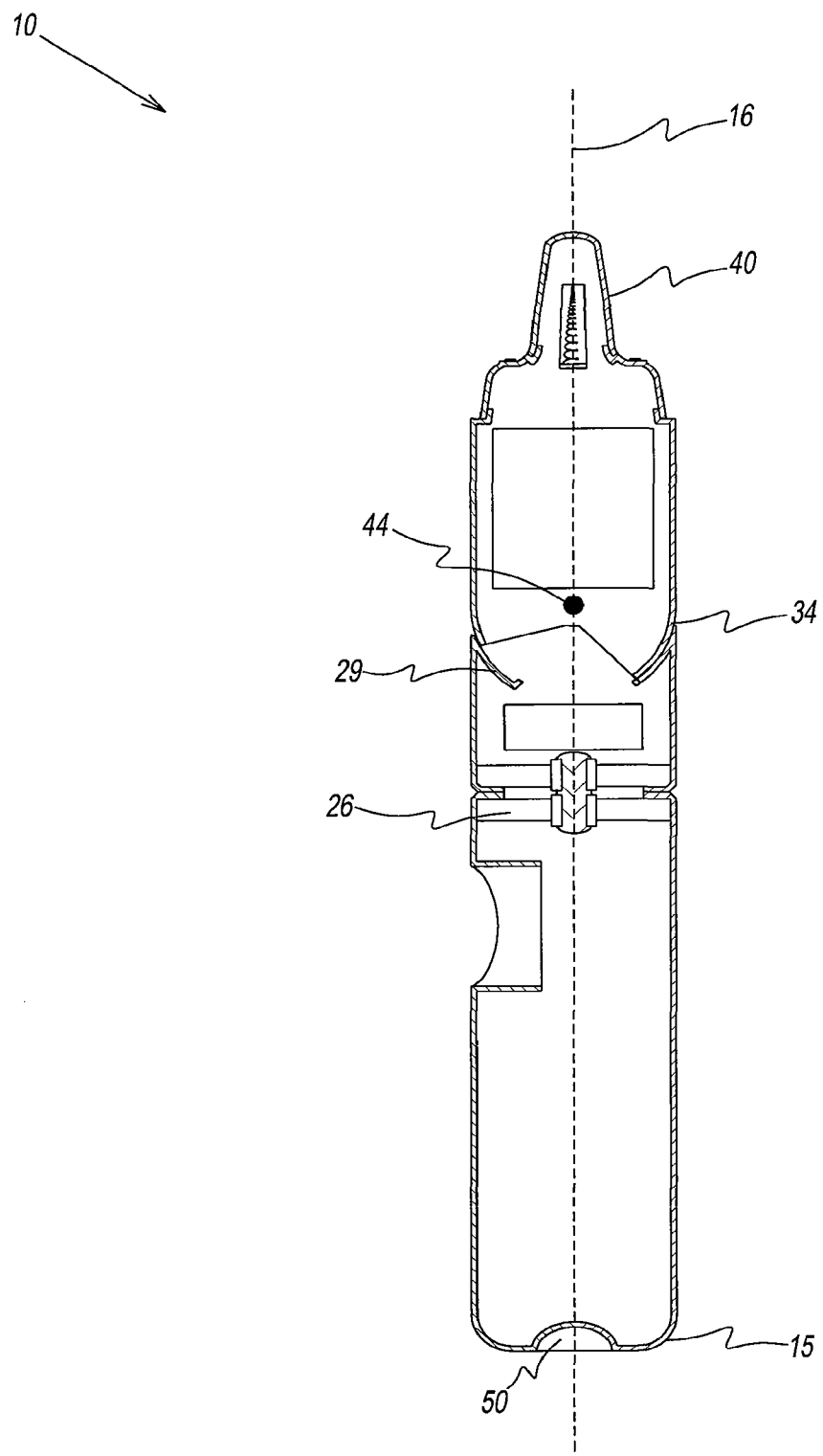
FIG. 4b is a partial cross-section of a rendition taken along line 4b-4b of the device of FIG. 1.
Figure 4C:
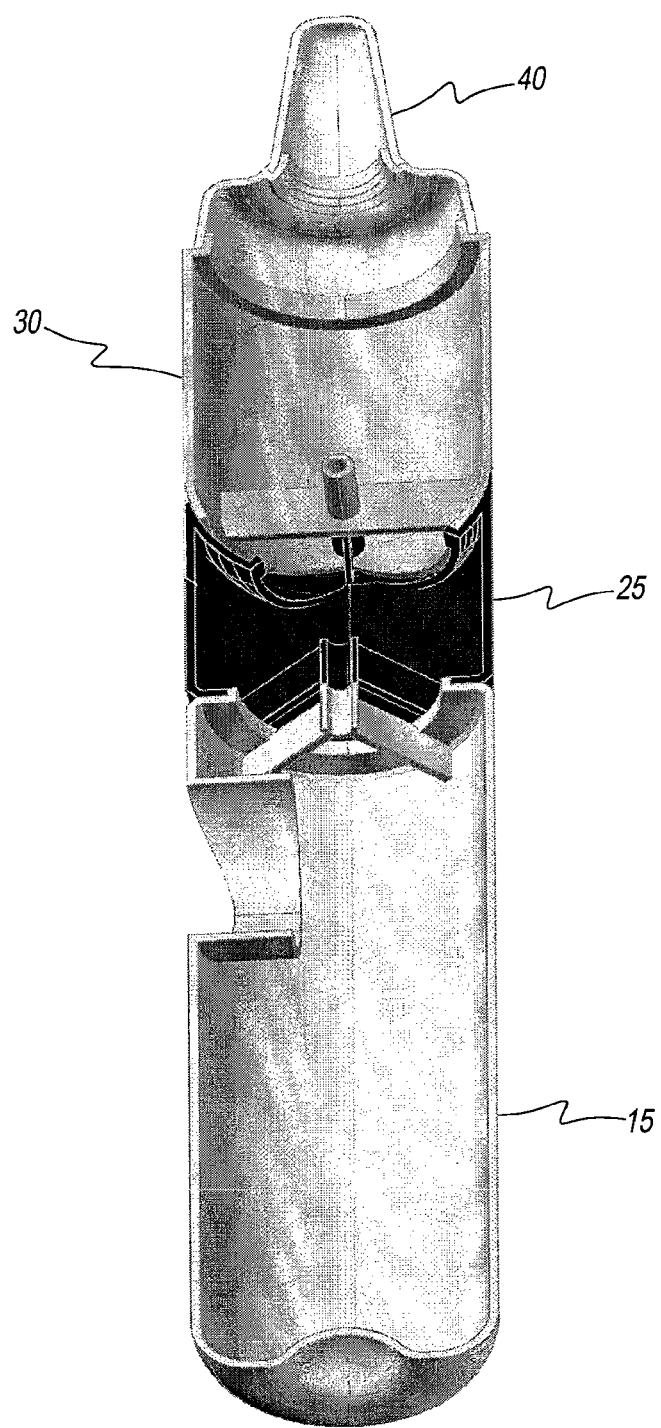
FIG. 4c is a partial cross-section of a rendition of the device of FIG. 1, showing the axial rotation mechanism.

FIG. 3 shows device 10 having a safety cap 45 positioned over insertion tip 40 and secured to endpiece 30 to protect insertion tip 40 from damage. At opposite end of device 10 from safety cap 45, base 15 has a charging coupling 50, as shown in FIG. 4a. Charging coupling 50 permits device 10 to be charged periodically via a power source such as a re-chargeable battery 18 by insertion into an induction charging unit (not shown) to maintain power in device 10 for adequate operation when needed.

Referring to FIG. 4a, device 10 has insertion tip 40, is shown. Insertion tip 40 is made from a medical grade transparent plastic that can withstand repeated exposure from light source 70. Transparent plastic permits a maximum amount of light emitted from light source 70 to be delivered to tissue of nasal cavity. Were insertion tip 40 made from a material that is opaque, the amount of light that would be delivered to tissue of nasal cavity for treatment would be lessened and optimal efficacy would not be achieved. Further, the material of insertion tip 40 acts as a filter to only permit light between predetermined wavelengths to be transmitted. When the light source 70 is a flashlamp, a wavelength of from 600 nm to about 690 nm can be used although a range of from 650 nm to 660 nm is preferred. Accordingly, insertion tip 40 will be constructed of a plastic that permits light in a wavelength of from 600 nm to 690 nm or 600 nm to 660 nm to pass therethrough. When light source 70 is a infra-red light is used a range of from about 700 nm to 950 nm can be used although a range of from 700 nm to 900 nm is preferred. Accordingly, insertion tip 40 will be constructed of a plastic that permits light in a wavelength of from about 700 nm to 950 nm, and preferably from 700 nm to 900 nm to pass therethrough. Insertion tip 40 may be connected to a surround 48 or insertion tip 40 and surround 80 may be unitary in construction.

Figure 5:
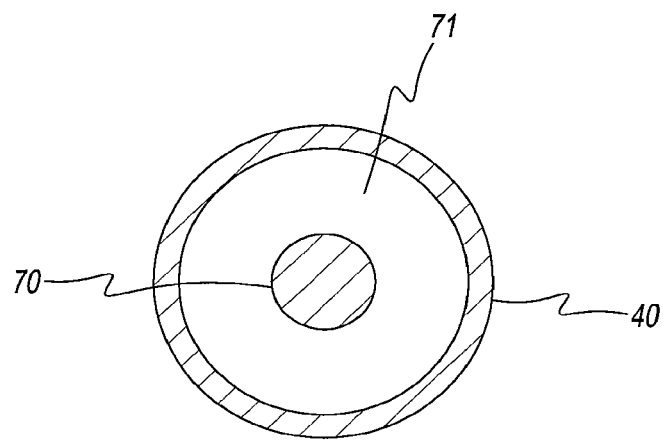
FIG. 5 is a cross-section view of the device of FIG. 1, taken along line 5-5.

Referring to FIG. 5, insertion tip 40 has an air cavity 71 between light source 70 and inner surface of insertion tip 40. Air cavity 71 functions as an insulator and prevents damage to sensitive tissue of nasal cavity. Air cavity exists around light source and has a thickness of from 2 mm to 5 mm. Air cavity may 71 may contain a gas, such as xenon, for purposes of illumination.

Figure 6:
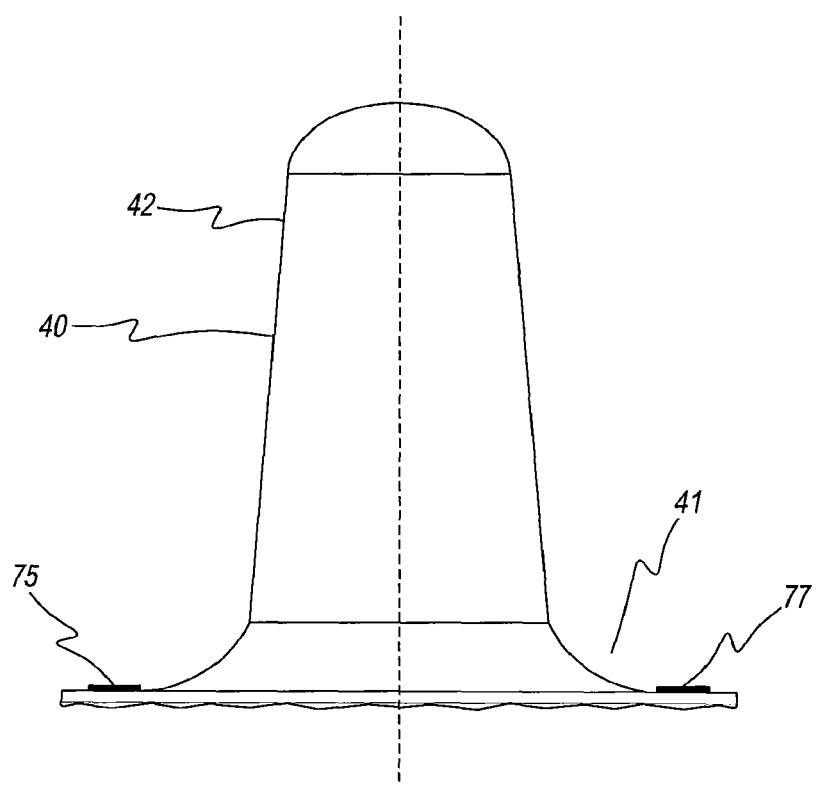
FIG. 6 illustrates a schematic view of the nasal tip of the device of FIG. 1.
Figure 7A:
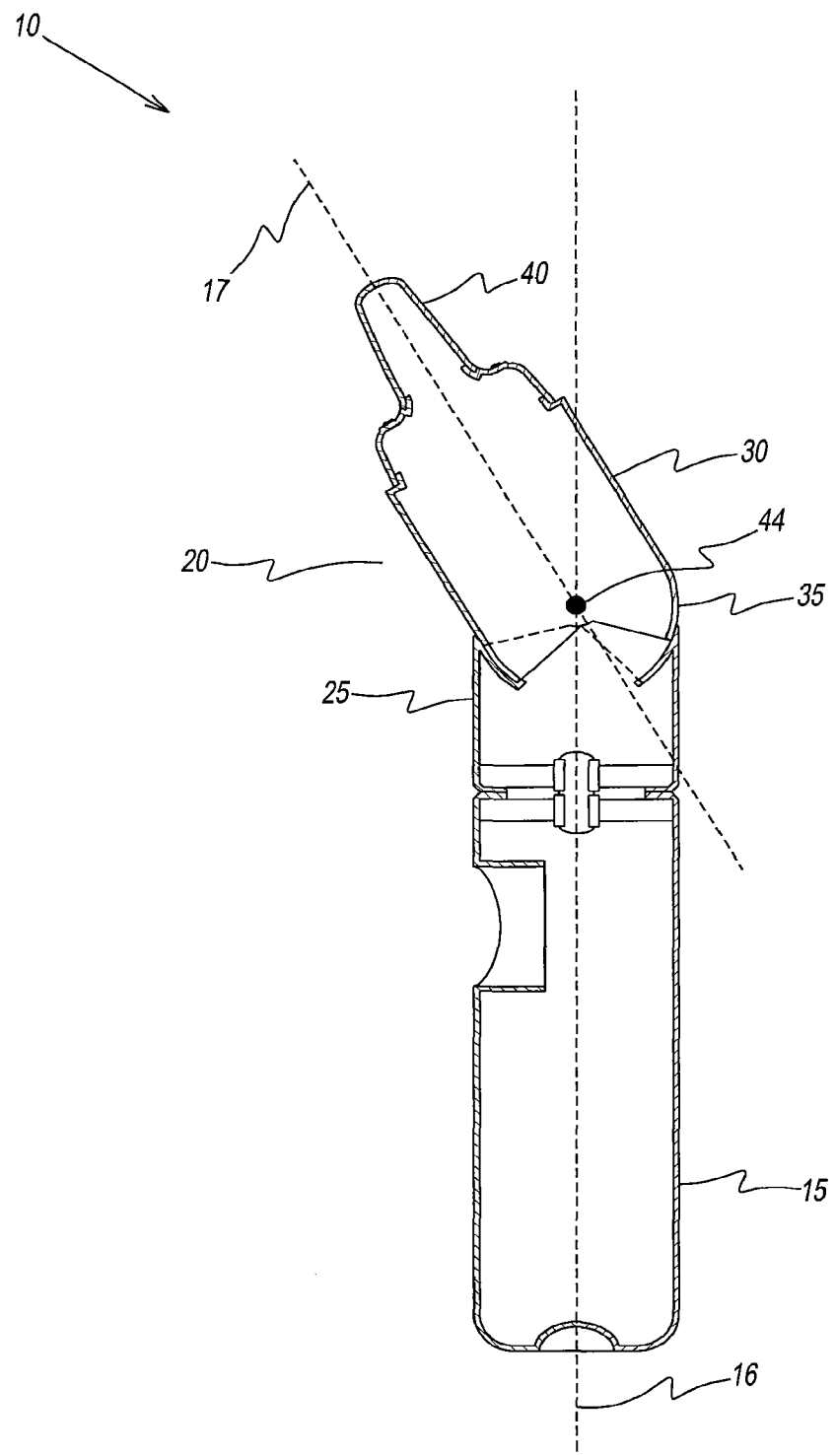
FIG. 7a is the device of FIG. 4, with the device in an angled configuration.
Figure 7B:
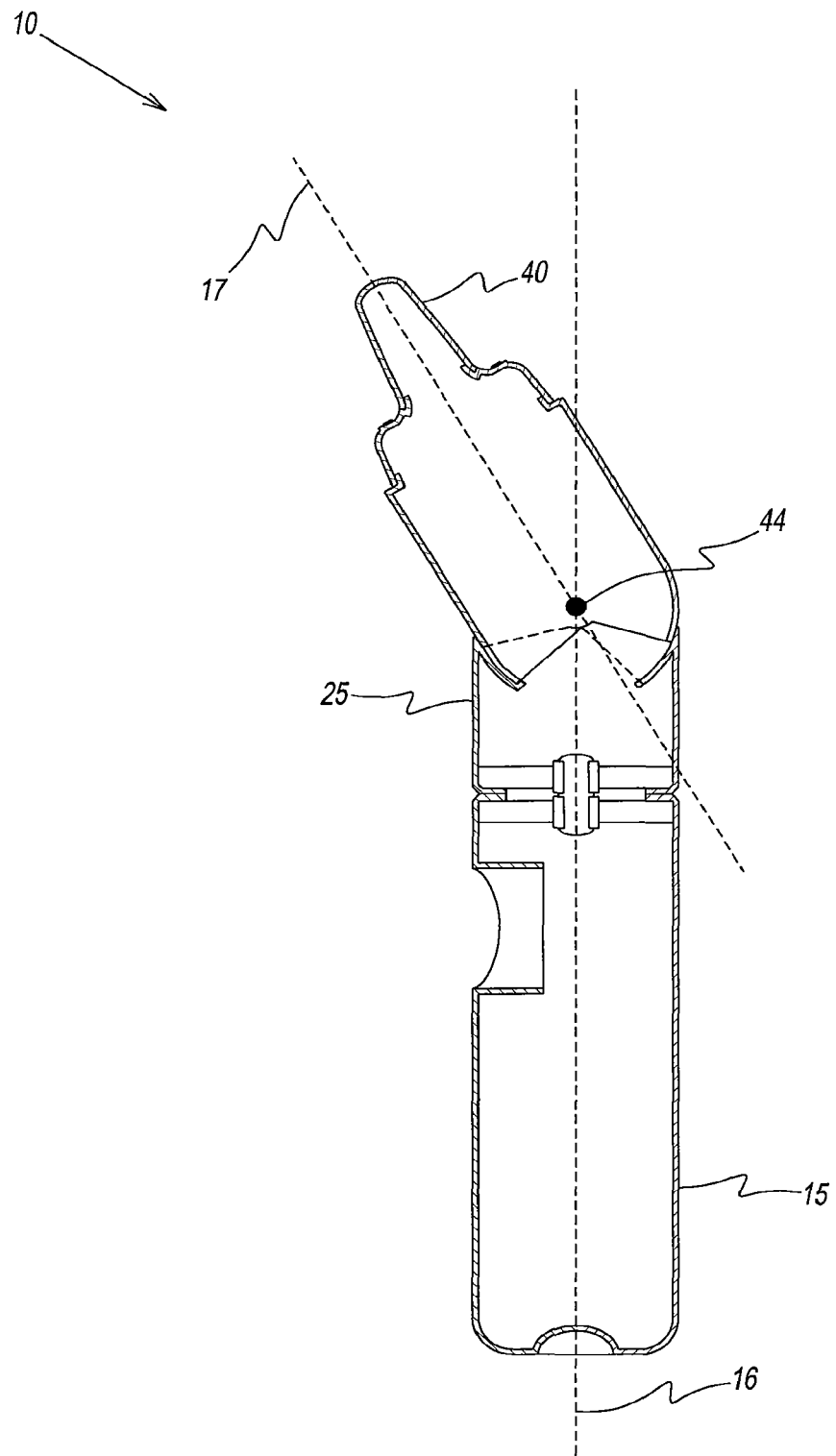
Figure 7C:
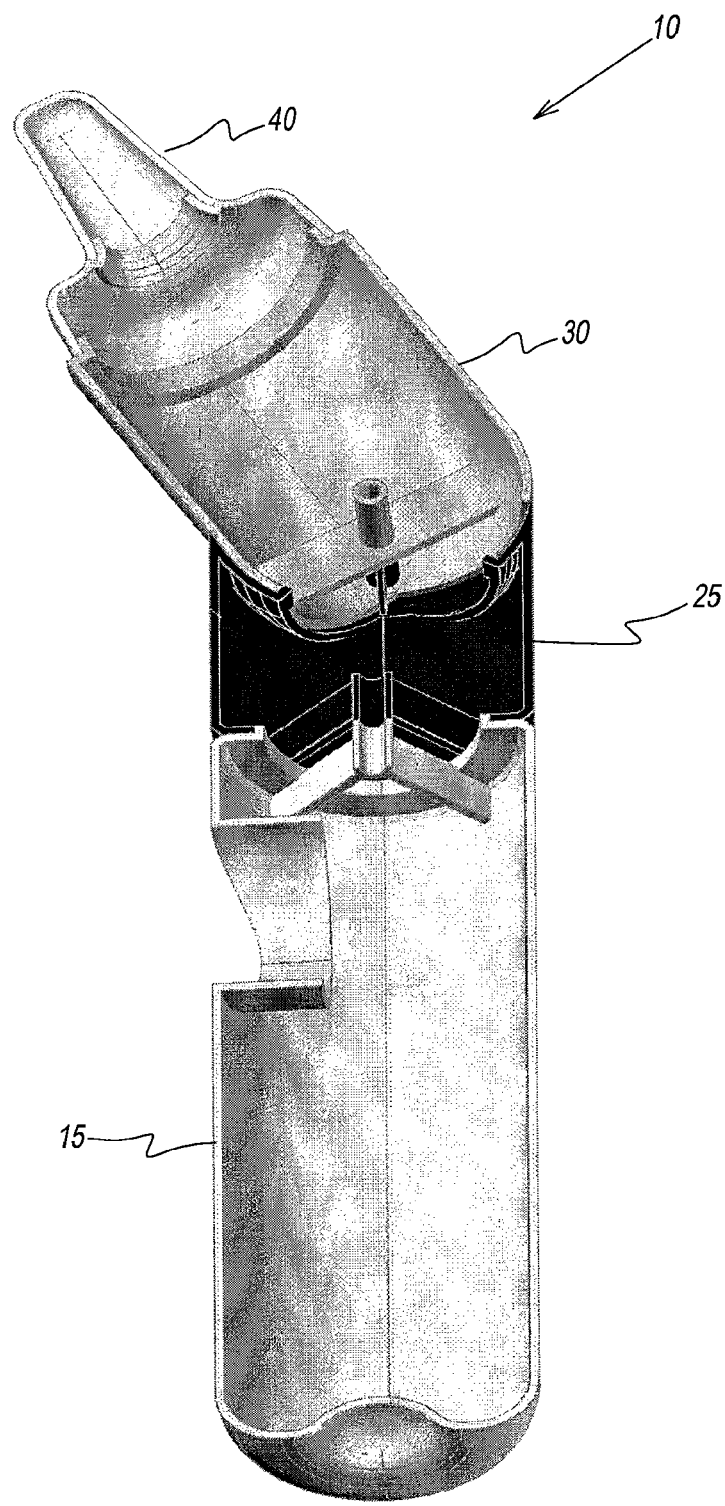
Figure 7D:
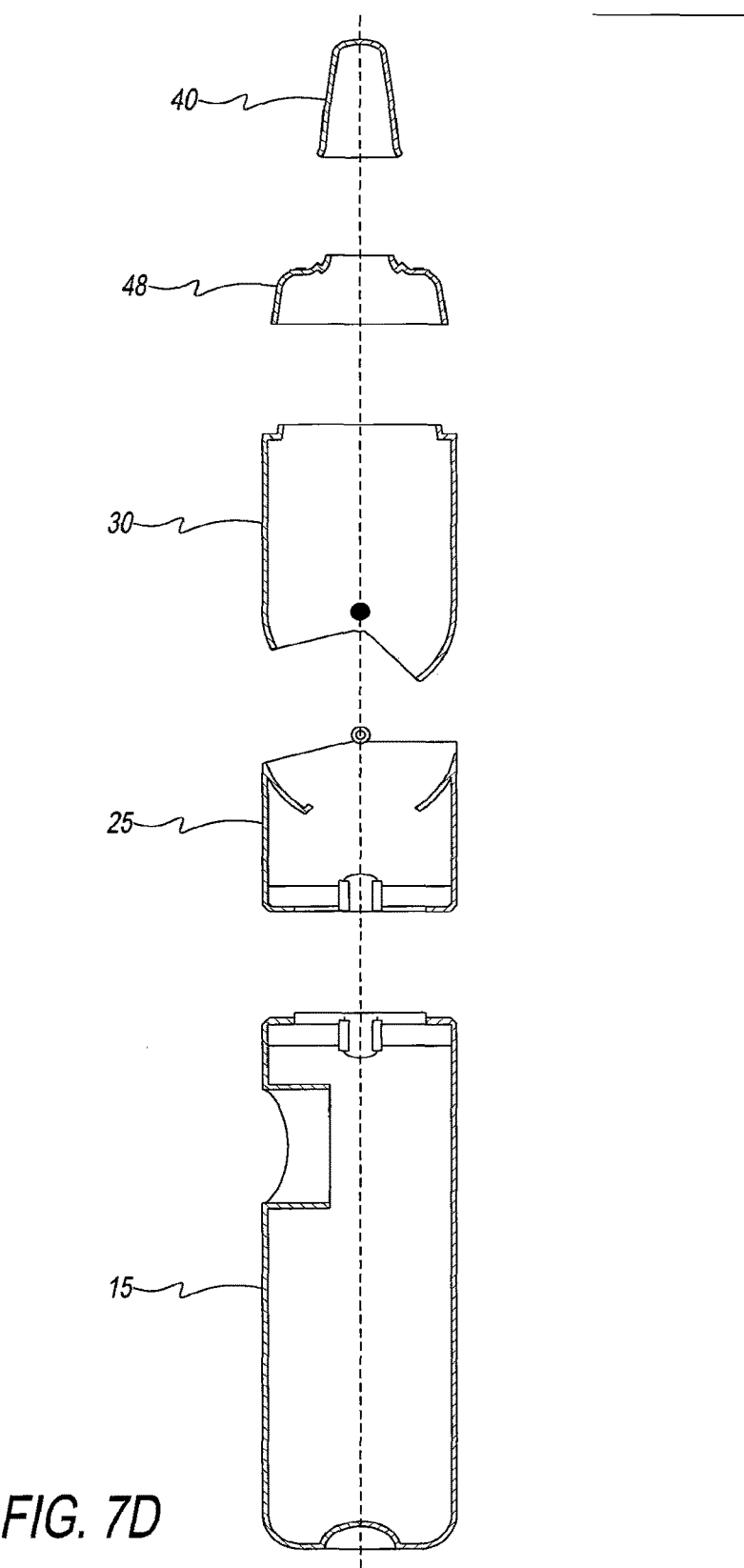

Referring to FIG. 6, insertion tip 40 is tapered from a tip base 41 to tip end 42. Insertion tip 40 ranges in length from approximately 0.6 to 1.0 inches (15.24 mm to 25.40 mm). Tip base 41 has a diameter of approximately 0.3 to 0.5 inches (7.63 mm to 12.70 mm), and tip end 42 has a diameter of from 0.22 to 0.3 inches (5.58 mm to 7.62 mm). These ranges of dimensions ensure that insertion tip 40 will have optimal contact with engorged or enflamed tissue in an individual suffering from seasonal allergies. Further, tip end 42 has a radius of 0.06 in to 0.12 inches (1.52 mm to 3.05 mm) to ensure comfort during use.

Referring to FIG. 4a, device 10 has a longitudinal axis 16 that extends from base 15 through sleeve 25 to insertion tip 40. FIG. 7 shows adjustable portion 20 and, in particular, endpiece 30 at an angle relative to sleeve 25. In the angled configuration, endpiece 30 has a longitudinal axis 17 that has an angle of 30 degrees relative to longitudinal axis 16 of base 15 and sleeve 25. Endpiece 30 can be positioned by user at any angle from 0° to 40° to achieve the most comfortable angle for positioning inside of the nasal cavity. Angles between 10° to 30° represent a mid-range of use for users and angles from 25° to 30° are optimal for comfort and efficacy. Sleeve 25 is a substantially hollow member that is pivotally fixed to endpiece 30 at pivot points 44. Endpiece 30 has a curved end 35 that moves in sleeve 25 during pivoting movement about pivot points 44 to change angle between sleeve 25 and endpiece 30. Endpiece 30 is maintained at angle in sleeve 25 by friction between endpiece surface 34 and sleeve surface 29.

Contained within endpiece 30 is light source 70, as shown in FIG. 4a. Light source 70 is shown as being a flashlamp, such as a xenon flashlamp, although other light sources 70, such as an infra-red light, an LED, fiber optic cable, or a laser could be used. For any embodiment of the light source, the power density of the delivered light is 12 to 24 joules/$cm^2$. When light is delivered at this power density through insertion tip 40 into the nasal cavity of a user, treatment of rhinitis and seasonal nasal allergies is achieved. Light source 70 has a longitudinal axis that coincides with longitudinally axis 17 of insertion tip 40. The coincident axes ensure optimal placement of light source relative to insertion tip 40 provide circumferential delivery of light to nasal tissue to light source 70. If light source was placed in an alternative fashion, circumferential delivery of light would not be achieved and optimal phototherapy treatment would be compromised.

Figure 8:
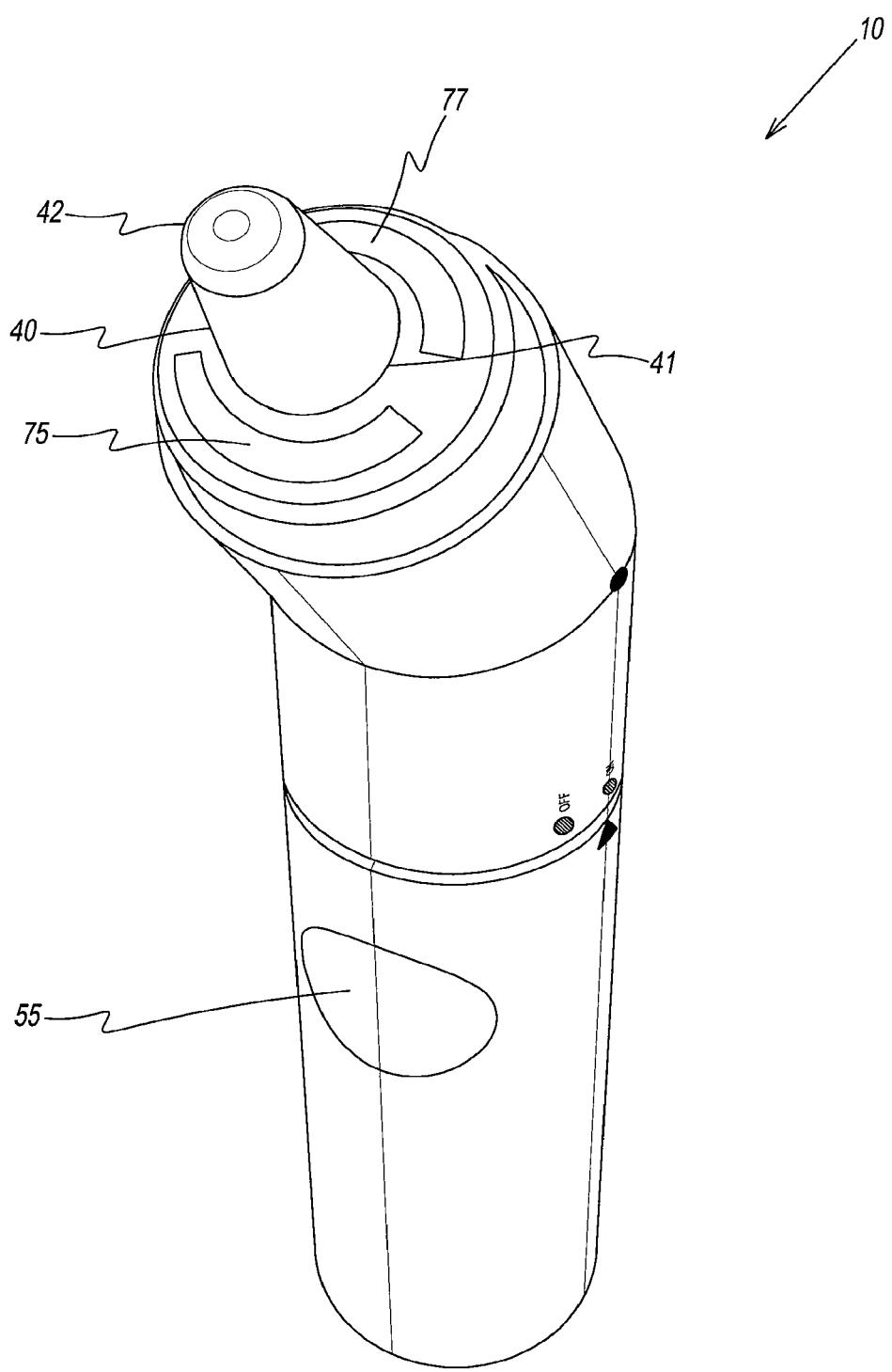
FIG. 8 is a front perspective view of the device of FIG. 1.
Figure 9:
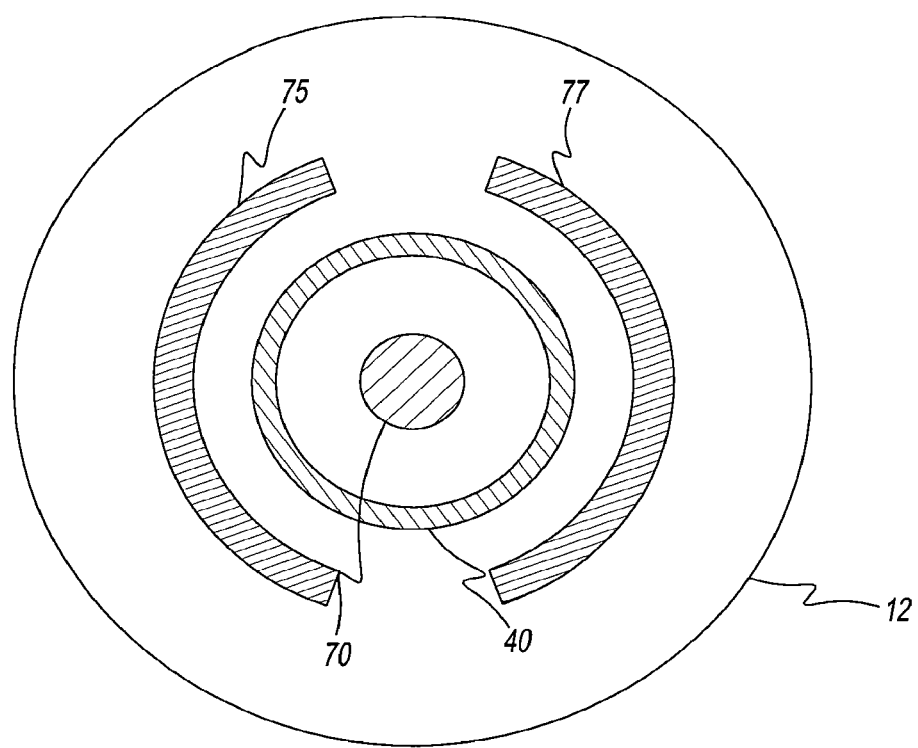
FIG. 9 is a top view of the device of FIG. 2.

Referring to FIGS. 4a, 8 and 9, insertion tip contains safety contacts 75, 77 proximate to tip base 41. Safety contacts 75, 77 are arcuate and almost semi-circular in configuration. Safety contacts 75, 77 contact outer surface of nostril to enable light to illuminate. Contacts 75, 77 are impedance sensors and actual contact between skin around nostril opening completes a circuit to permit light source to be activated by depressing trigger 55. With impedance sensors 75, 77, if the skin on both sides of nostril is not in contact with sensors, light source will not illuminate insertion tip 40. Impedance sensors 75, 77 have an arcuate and almost semi-circular shape to correspond to the outer surface of nostril.

Alternatively, when safety contacts 75, 77 are depressed during insertion into nasal cavity, a circuit is completed that permits light source to be activated by depressing trigger 55. If safety contacts 75, 77 are both not depressed, light will not be illuminated. Safety contacts 75, 77 ensure that light source will not be accidently activated with depression of trigger 55, until insertion tip 40 is inserted and in contact with outer surface of nostril. Accidental exposure to light from light source 70 could damage the eyes of user or those of a nearby individual. Significantly, each safety contacts 75, 77 has an arcuate and almost semicircular shape to correspond to the outer surface of nostril.

Alternatively, contacts 75, 77 are impedance sensors and actual contact between skin around nostril opening completes a circuit to permit light source to be activated by depressing trigger 55. With impedance sensors 75, 77, if the skin on both sides of nostril is not in contact with sensors, light source will not illuminate insertion tip 40. Impedance sensors 75, 77 have an arcuate and almost semi-circular shape to correspond to the outer surface of nostril.

Figure 10:
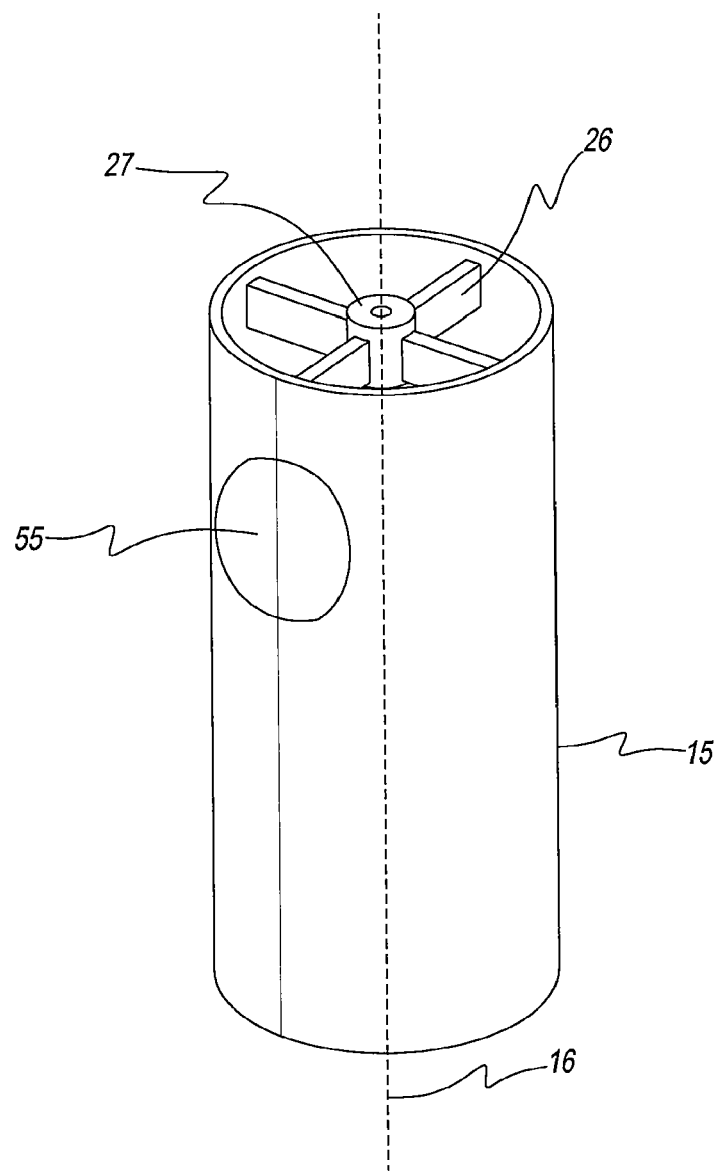
FIG. 10 is a perspective view of the base of the device of FIG. 1.

Referring again to FIGS. 2 through 4 and FIG. 10, base 15 is rotatable relative to sleeve 25 of adjustable portion 20 around longitudinal axis 16 of base 15. By rotating base 15 relative to sleeve 25, device 10 is changed from a powered position (FIG. 2) to an unpowered position (FIG. 3). The relative rotational movement from powered to unpowered position provides contact electrical between power source 18 and transformer 19 in sleeve 25. FIGS. 4 and 10 show pin 24 and pin supports 26 and support channel in base 15 (shown) and sleeve 25, respectively that permits relative rotational movement. Base 15 also has a trigger 55 that is depressed to enable light source 70 to be activated.

Figure 11:
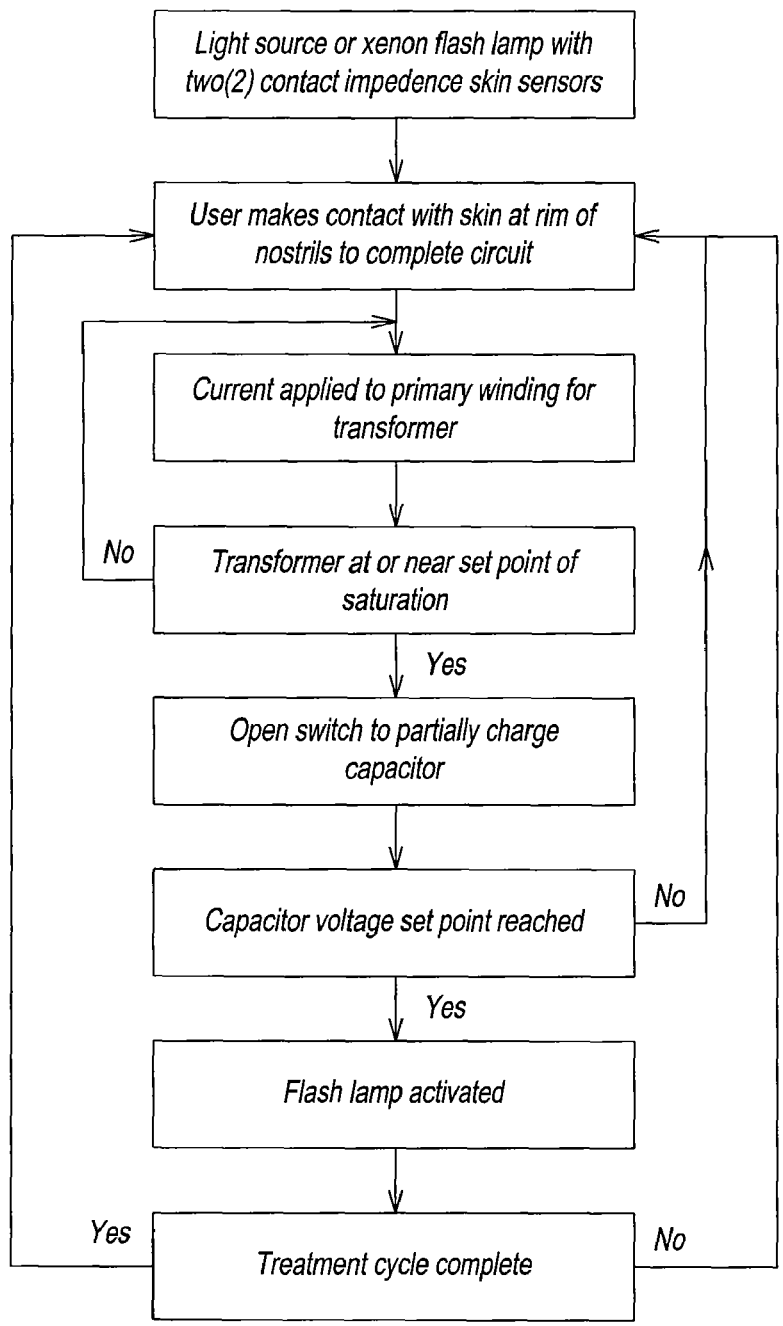
FIG. 11 is a flowchart illustrates methodology of using the device of FIG. 1.

During operation as shown in flowchart of FIG. 11, a user is able to power device 10 by rotating base 15 relative to sleeve 25, to provide electrical contact between chargeable battery 18 and transformer 19. A voltage develops across transformer 19 which builds an electrical charge in capacitor 23. When user places insertion tip 40 into nasal cavity and makes contact between skin at rim of nostrils and contacts 75, 77, a circuit is completed in board 27. Current is applied to primary winding of transformer. By completing circuit, trigger 55 is operable to administer phototherapy. If transformer 19 is at or near a set point of saturation, open switch to partially charge capacitor. Once capacitor voltage has reached set point, light source 70 is activated. Depression of trigger 55 discharges capacitor 23 and a circuit in board 27 delivers a high-voltage pulse to light source 70 that initiates a current flow in insertion tip 40. Device 10 is fully self-contained within housing 12 and a re-chargeable battery powers the control circuitry. Control circuitry contains either a logic circuit or suitable software to charge electrical system and to deliver a desired amount of illumination to nasal cavity. Light source 70 is controlled by circuitry to deliver approximately 12 to 24 Joules/cm$^2$ to nasal cavity of user. This dosage provides the desired efficacy without damaging or causing discomfort to the patient.

The present device 10 stimulates the human body's own respiratory system to reduce symptoms of allergic rhinitis. The typical human allergic response in the respiratory tract is characterized by two phases of the immune system. In the initial phase, after an allergen challenge is presented to the body (e.g. via the inhalation of dust, pollen, dust, or other allergens), resident mast cells in the nose and bronchi degranulate to release histamine as well as other vasoactive mediators (such as prostaglandins, leukotriens, etc.). These mediators typically cause localized itching and swelling of tissue, as well as an increase in the mucous production.

In a second phase of the allergic response, a myriad of inflammatory cells (such as activated T cell, eosinophils and basophils) are recruited to the inflammatory site. These inflammatory cells further inflame the local tissues, and typically perpetuate the inflammatory response for as long as the allergen is present. Allergy sufferers are familiar with these symptoms (itching and swelling of tissues, increased mucus production, etc.).

Studies have shown that those phases of the allergic response can be beneficially inhibited (to relieve the allergy sufferer) by the application of phototherapy, and that phototherapy can have profound immunosuppressive effects in such applications. In one such study, phototherapy significantly reduced the number of eosinophils and T cells by inducing apoptosis through a light-mediated alteration in Ca+ metabolism within these cells. Furthermore, phototherapy inhibited the release of histamines from basophils and mast cells. In short, these studies indicate that application of phototherapy can improve clinical symptoms such as sneezing, rhinorrhea (runny nose), nasal itching, and nasal congestion.

Thus, the present device 10 can be used to provide the desired phototherapy in the treatment of allergic rhinitis.

It should be understood that the foregoing description is only illustrative of the present disclosure. Various alternatives and modifications can be devices by those skilled in the art without departing from the disclosure. Accordingly, the present disclosure is intended to embrace all such alternatives, modification and variances that fall within the scope of the present disclosure.

I claim:

1. A device for delivering light to a nasal cavity, the device having a longitudinal device axis, the device comprising:
   a base having a trigger, a first end that is a proximal end, and a second end opposite the first end that is a distal end, wherein the distal end has a first pin support;
   a power source that can be disposed in the base;
   a sleeve having a first end and a second end, the first end having a second pin support;
   a pin coincident with the device axis and received by the first pin support and the second pin support to join the base and the sleeve, wherein the base and the sleeve are rotatable about the device axis between a first position and a second position;
   an endpiece that has an endpiece axis extending longitudinally therethrough, the endpiece connected to the sleeve at a pivot joint at the second end of the sleeve,
   a tapered insertion tip connected to the endpiece at an end opposite the sleeve, wherein the tapered insertion tip is insertable into the nasal cavity, a light source disposed in the tapered insertion tip so that at least a portion of the light source is inserted into the nasal cavity during operation of the device, wherein the device axis extends from the base through the sleeve and the endpiece to the insertion tip;

wherein the endpiece pivots relative to the sleeve so that an angle between the device axis and the endpiece axis is adjustable in a range from 0° to 40°, and wherein the angle is maintained by a friction fit between a surface of the endpiece and a surface of the sleeve, and;

wherein the trigger on the base is inoperable to activate the light source when the sleeve and the base are rotated to the first position and is operable when the sleeve and the base are rotated to the second positions.

2. The device according to claim 1, wherein the angle is about 0° to 30°.

3. The device according to claim 1, wherein the angle is from 10° to 30°.

4. The device according to claim 1, wherein the angle is from 25° to 30°.

5. The device according to claim 1, wherein the tapered insertion tip has an air cavity comprising xenon gas for providing insulation between the light source and an inner surface of the tapered insertion tip.

6. The device according to claim 5, wherein the air cavity has a thickness of from 2 mm to 5 mm and the light source is a xenon flash lamp.

7. The device according to claim 1, wherein the tapered insertion tip has a length that ranges from approximately 0.6 to 1.0 inches.

8. The device according to claim 1, further comprising:
a charging coupling connected to the power source; and
an induction charging unit, wherein the charging coupling is adapted for insertion into the induction charging unit to recharge the power source.

9. The device according to claim 1, wherein the light source is selected from the group consisting of: a flashlamp, a light emitting diode (LED), a fiber optic cable, and a laser beam.

10. The device according to claim 9, wherein the light source is a flashlamp and has a wavelength in a range of from 600 nm to about 690 nm.

11. The device according to claim 1, wherein the light source is an infra-red light and has a wavelength in a range of from 700 nm to 950 nm.

12. The device according to claim 1, wherein the light source provides light in a wavelength of from 600 to 650 nm at a power of from 12 to 24 Joules/cm$^2$.

13. The device according to claim 1, further comprising a transformer, a capacitor and a circuit board operably connected to the trigger, whereby rotation of the base and sleeve to the second position completes a circuit to charge the capacitor and depression of the trigger discharges the capacitor so that the circuit board delivers a high-voltage pulse to the light source and initiates a current flow in the tapered insertion tip.

14. The device according to claim 13, wherein the endpiece comprises a pressure sensor that detects pressure between the pressure sensor and an outer rim of a nostril of the nasal cavity when the tapered insertion tip is inserted into the nasal cavity, and wherein the pressure sensor enables illumination of the light source when pressure is detected and prevents illumination of the light source when pressure is not detected.

15. The device according to claim 13, wherein the endpiece comprises an impedance sensor that detects contact between the impedance sensor and an outer rim of a nostril of the nasal cavity when the tapered insertion tip is inserted into the nasal cavity to enable illumination of the light source and prevents illumination of the light source when contact is not detected.

16. The device according to claim 1, wherein the taper of the tapered insertion tip is from a range of 0.3 to 0.5 inches at a base to a range of 0.22 to 0.3 inches at an end.

17. The device according to claim 1, wherein the tapered insertion tip has a tip end that has a radius of 0.06 to 0.12 inches.

18. The device according to claim 1, wherein the light source has a light source axis that coincides with the endpiece axis to provide circumferential delivery of light.

19. The device according to claim 1, wherein the tapered insertion tip filters light so that only light in wavelengths between 600 nm and 950 nm is transmitted therethrough.

20. The device according to claim 1, wherein the endpiece pivots at a point coincident with the device axis.

* * * * *